United States Patent [19]

Ginsburg et al.

[11] 4,249,018
[45] Feb. 3, 1981

[54] SYNTHESIS OF CITRIC ACID OR CITRATES

[75] Inventors: David Ginsburg, Haifa, Israel; Wilfried J. W. Mayer, Stuttgart, Fed. Rep. of Germany; Allan Wexler, Mountaindale, N.Y.

[73] Assignee: Miles Laboratories, Inc., Elkhart, Ind.

[21] Appl. No.: 70,136

[22] Filed: Aug. 27, 1979

[51] Int. Cl.$^3$ .................. C07C 59/265; C07C 69/704
[52] U.S. Cl. ..................................... 560/180; 562/584
[58] Field of Search ............... 560/180; 562/584, 529, 562/528, 544; 260/465.4

[56] References Cited

U.S. PATENT DOCUMENTS

| 3,503,997 | 3/1970 | Fields | 260/465.4 |
|---|---|---|---|
| 3,770,796 | 11/1973 | Lawrence et al. | 562/584 |
| 3,950,390 | 4/1976 | Faubl | 562/504 |

OTHER PUBLICATIONS

Grob, C. A. et al., "Cyclodecapolyenes . . . ", *Helv. Chim. Acta.* 43, pp. 1546–1555, (1960). See Chemical Abstracts, vol. 55, (1961), # 7607b.

Noller, Carl R., *Chemistry of Organic Compounds*, (1957), 2nd Ed., p. 266.

*Primary Examiner*—Joseph E. Evans
*Assistant Examiner*—L. Hendriksen
*Attorney, Agent, or Firm*—Louis E. Davidson

[57] ABSTRACT

Citric acid or a citrate ester can be prepared by the process comprising the steps of oxidizing isotetralin to form cyclodeca-1,6-diene-4,9-dione, converting the dione into the bis-cyanohydrin derivative, ozonating the bis-cyanohydrin and recovering citric acid or a citrate ester. It is preferred that the isotetralin be prepared by reduction of naphthalene.

2 Claims, No Drawings

SYNTHESIS OF CITRIC ACID OR CITRATES

BACKGROUND AND PRIOR ART

Citric acid is a well-known item of commerce. It is generally produced by the selective fermentation of carbohydrates or hydrocarbons using fungi or yeasts. Various organic syntheses of citric acid have been proposed in recent years. Representative prior art on such organic syntheses are U.S. Pat. Nos. 3,356,721, 3,755,436, 3,769,337, 3,769,338, 3,770,796, 3,783,154, 3,798,266, 3,852,322, 3,912,778, 3,917,686, 3,950,390, 3,950,397, 3,962,287, 4,022,823, 4,056,567, 4,066,688, 4,079,088, 4,113,771 and 4,139,556. None of these prior art processes employ isotetralin as a starting material. Since isotetralin can be obtained from naphthalene, none of these prior art processes disclose the use of readily available naphthalene as a starting material.

SUMMARY OF THE INVENTION

In accordance with the present invention, a process for the production of citric acid or a citrate ester is provided which comprises the steps of oxidizing isotetralin to form cyclodeca-1,6-diene-4,9-dione, converting the dione into the bis-cyanohydrin derivative, ozonating the bis-cyanohydrin and recovering citric acid or a citrate ester. Preferably, the isotetralin is obtained by reduction of naphthalene.

DESCRIPTION OF THE INVENTION

The isotetralin used as a raw material for the production of citric acid or a citrate ester is well-known. It is known to be produced by reduction of naphthalene using sodium in liquid ammonia.

The overall process of the present invention is illustrated by the following reaction sequence:

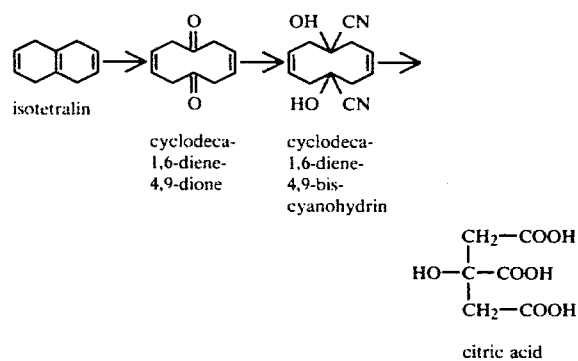

In the first step of this novel process, the isotetralin is oxidized to form cyclodeca-1,6-diene-4,9-dione. There are various alternative procedures for accomplishing this conversion. One procedure involves the step-wise conversion of the isotetralin into 9,10-epoxy-1,4,5,8,9,10-hexahydronaphthalene, conversion of the epoxy derivative into trans-9,10-dihydroxy-1,4,5,8,9,10-hexahydronaphthalene, and conversion of the trans-dihydroxy derivative into the dione. This is shown step-wise in the following reaction sequence:

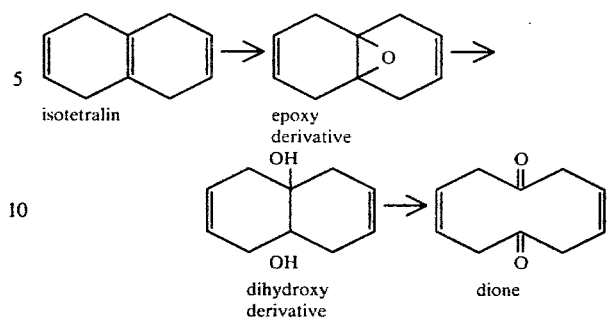

The epoxy derivative can be produced by reaction of isotetralin with perbenzoic acid in chloroform solvent at a temperature at or slightly above 0° C. Conversion of the epoxy derivative into the trans-dihydroxy derivature can be accomplished by step-wise reaction with acetic acid followed by potassium hydroxide at 90° C. The trans-dihydroxy derivative can be converted into the dione by use of a mixture of trichloroacetic acid, dimethoxyethane and lead tetraacetate at 20° C. In the above formula and elsewhere in this specification relating to "trans" compounds, the dashed line ( - - - ) represents a bond that is below the structural plane of the compound. The solid line (—) for the opposing hydroxyl group represents a bond that is above the structural plane of the compound.

An alternate procedure for production of the dione involves production of the above epoxy derivative, conversion of the epoxy derivative into a trans-9-hydroxy-10-peroxy derivative, such as trans-9-hydroxy-10-hydro-peroxy-1,4,5,8,9,10-hexahydronaphthalene or trans-9-hydroxy-10-t-butylperoxy-1,4,5,8,9,10-hexahydronaphthalene, and conversion of such trans-9-hydroxy-10-peroxy derivative into the dione. This is shown by the following reaction sequence:

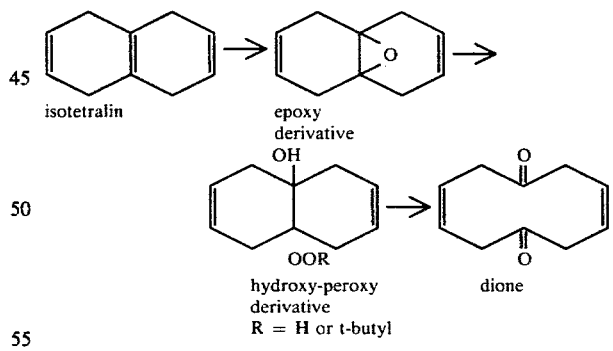

Conversion of the epoxy derivative into the trans-9-hydroxy-10-peroxy derivative can be accomplished by use of hydrogen peroxide or t-butylhydroperoxide in ether plus boron trifluoride-etherate or p-toluenesulfonic acid. The trans-9-hydroxy-10-peroxy derivative can be converted into the dione by trifluoracetic acid or boron trifluoride in ether. Alternatively, the reaction conditions given above for conversion of the trans-dihydroxy derivative into the dione can also be used.

In still another process variation, the above epoxy derivative can be converted directly into the dione by reaction in dioxane with p-toluenesulfonic acid and hydrogen peroxide followed by treatment with trifluoroacetic acid.

The dione is converted into the bis-cyanohydrin derivative by a mixture of acetone cyanohydrin and potassium carbonate in methanol at room temperature. The bis-cyanohydrin derivative is then converted into citric acid by step-wise ozonolysis at $-65$ to $-78°$ C. in methanol, followed by treatment with hydrogen peroxide at $0°$ C. and ethereal diazomethane at room temperature. The citric acid is conveniently recovered as a citrate ester, such as tri-methyl citrate, by crystallization from an alcohol solution, such as methanol. Purified citric acid can be easily produced by acidulation of the citrate.

The invention is described in further detail in the following examples.

EXAMPLE I

A 64 g. portion (0.49 mole) of isotetralin (previously produced by reduction of naphthalene) dissolved in 300 ml. chloroform was mixed with 850 ml. of a chloroform solution of perbenzoic acid containing 0.54 mole perbenzoic acid. The perbenzoic acid solution was added in a slow stream during a 0.5 hr. period at a temperature slightly above $0°$ C. The resulting mixture was then stirred while warming to room temperature. The reaction mixture was then extracted with a 20 weight percent aqueous solution of sodium hydroxide to remove any unreacted perbenzoic acid. The aqueous phase was discarded. The chloroform phase was then concentrated and dried on a thin film evaporator under vacuum. The concentrated residue was then dissolved in a mixture of hexanes and filtered to remove a small amount of solids. The resulting solution was then cooled with a solid carbon dioxide-isopropanol bath and the precipitated crystals thus formed were removed by filtration. These crystals were redissolved in a mixture of hexanes and recrystallized to yield 24 g. (0.16 mole) of 9,10-epoxy-1,4,5,8,9,10-hexahydronaphthalene. It had a melting point of $64°-65°$ C.

The above-prepared epoxy derivative was stirred for 2 hr. at $90°$ C. in 220 ml. of a 10 weight percent aqueous solution of acetic acid. The mixture was cooled to $3°$ C. The resulting precipitated crystals were filtered, washed twice with ice water and stirred for 2 hr. at $90°$ C. in 220 ml. of 1 N potassium hydroxide. The resulting mixture was cooled to room temperature and the product was filtered. The solids were dissolved and recrystallized from hot water, then dried in vacuum over phosphorus pentoxide yielding 24 g. of trans-9,10-dihydroxy-1,4,5,8,9,10-hexahydronaphthalene. It had a melting point of $80°-83°$ C.

A 10.5 g. portion (0.063 mole) of the above trans-dihydroxy derivative was stirred at about $20°$ C. with 31 g. of trichloroacetic acid in 250 ml. dimethoxyethane while 42 g. (0.092 mole) of lead tetraacetate were slowly added. The resulting reaction mixture was then stirred 4 hr. at room temperature. A few ml. of ethylene glycol were added to react with any excess lead tetraacetate. The resulting mixture was cooled to $-65°$ C. The dark colored product was filtered, redissolved in hot acetone and filtered to remove a small amount of undesirable dark colored solids. The water-white filtrate produced white crystals upon cooling with ice water. The crystals were filtered and dried to yield 5.5 g. of cyclodeca-1,6-diene-4,9-dione having a melting point of $183°-186.5°$ C.

A 2 g. portion (0.0122 mole) of the above dione was stirred for 2 hr. at room temperature with 4.2 g. (0.05 mole) acetone cyanohydrin and 1.7 g. (0.0123 mole) potassium carbonate in 6.1 ml. methanol. Twenty-eight drops of 85 weight percent aqueous phosphoric acid were then added to the reaction mixture. The dark brown mixture was then stirred for 15 min. and concentrated in a thin film evaporator under vacuum. The solid residue was extracted with 700 ml. of boiling methylene chloride and the undissolved material was removed by filtration. The yellow filtrate was evaporated to dryness leaving 2 g. of brown solid bis-cyanohydrin derivative. The bis-cyanohydrin derivative was then dissolved in 50 ml. methanol and ozonated at $-65°$ C. for 1 hr. The reaction mixture was then warmed to room temperature under an argon stream yielding a light yellow solution which was then concentrated in a thin film evaporator under vacuum. The yellow syrup remaining was dissolved in 25 ml. formic acid and reacted at $0°$ C. with 25 ml. of 30 weight percent aqueous hydrogen peroxide. The resulting solution was stored for several hours at $0°$ C. and then allowed to warm slowly to room temperature with stirring overnight. The clear, almost colorless solution was warmed at $70°$ C. for 2 hr. and then concentrated in a thin film evaporator under vacuum to form an amber glass-like residue. This residue was dissolved in methanol and treated with excess ethereal diazomethane. A small amount of white sticky precipitate formed. The supernatant liquid was separated and concentrated to a light yellow oil kept overnight under high vacuum. This oil was then distilled in a Kugelrohr apparatus under vacuum at $90°$ C. to produce a yellow oil which crystallized. It was then recrystallized from methanol to yield 0.2 g. trimethyl citrate having a melting point of $77°-80°$ C. The identity of the trimethyl citrate was confirmed by gas chromatographic and nuclear magnetic resonance analyses.

Citric acid can be obtained by acidulation of the above trimethyl citrate.

Formation of the trans-9-hydroxy-10-t-butylperoxy derivative is described in the following example.

EXAMPLE 2

To a mixture of 444 mg. of 9,10-epoxy-1,4,5,8,9,10-hexahydronaphthalene prepared as in Example 1 above and 2.7 g. of t-butylhydroperoxide in 2 ml. anhydrous ether were added 50 mg. of p-toluenesulfonic acid. After 2 hr. stirring at room temperature the reaction mixture was extracted with 80 ml. chloroform, then with 50 ml. of 5 weight percent aqueous sodium bicarbonate and finally with 50 ml. saturated brine. It was then dried over sodium sulfate. The solvent was removed on a thin film evaporator under vacuum to produce 740 mg. of desired product oil which was identified as trans-9-hydroxy-10-t-butylperoxy-1,4,5,8,9,10-hexahydronaphthalene by nuclear magnetic resonance techniques.

This material can then be converted into the dione and subsequently to citric acid by procedures described in Example 1.

What is claimed is:

1. A process for the production of citric acid or a citrate ester comprising the steps of reducing naphthalene to isotetralin, converting the isotetralin to 9,10-epoxy-1,4,5,8,9,10-hexahydronaphthalene, converting the epoxy derivative into trans-9,10-dihydroxy-1,4,5,8,9,,10-hexahydronaphthalene, converting the trans-dihydroxy derivative into cyclodeca-1,6-diene-4,9-dione, converting the dione into the bis-cyanohydrin derivative, ozonating the bis-cyanohydrin derivative, reacting the ozonated derivative step-wise with hydrogen peroxide and diazomethane and recovering citric acid or a citrate ester.

2. A process for the production of citric acid or a citrate ester comprising the steps of reducing naphthalene to isotetralin, converting the isotetralin to 9,10,-epoxy-1,4,5,8,9,10-hexahydronaphthalene, converting the epoxy derivative into trans-9-hydroxy-10-t-butylperoxy-1,4,5,8,9,10-hexahydronaphthalene, converting the trans-9-hydroxy-10-peroxy derivative into cyclodeca-1,6-diene-4,9-dione, converting the dione into the bis-cyanohydrin derivative, ozonating the bis-cyanohydrin derivative, subsequently reacting the ozonated derivative step-wise with hydrogen peroxide and diazomethane and recovering citric acid or a citrate ester.

* * * * *